United States Patent [19]

Lampin, deceased et al.

[11] Patent Number: 4,859,797

[45] Date of Patent: Aug. 22, 1989

[54] NOVEL NON IONIC FLUORINATED COMPOUNDS, THEIR PROCESS OF PREPARATION AND APPLICATIONS THEREOF AS SURFACTANTS

[75] Inventors: Jean-Pierre Lampin, deceased, late of Moulignon Ponthierry; Jeannine Robillart Lampin, heir, Saint Fargeau Pontthierry; Corinne Lampin, heir, Saint Fargeau Pontthierry; Sophie Lampin, heir, Saint Fargeau Pontthierry; Aimé Cambon, Nice, all of France; Francois Szonyi, Monaco, Monaco; Jean-Jacques Delpuech, Laxou, France; Guy Serratrice, Villers les Nancy, France; Gérard Thiollet, Ballancourt, France; Louisette Lafosse, Vert le Petit, France

[73] Assignee: Institut National de Recherche Chimique Appliquee, Paris, France

[21] Appl. No.: 48,540

[22] Filed: May 6, 1987

Related U.S. Application Data

[63] Continuation of Ser. No. 738,701, May 29, 1985, abandoned.

[30] Foreign Application Priority Data

May 29, 1984 [FR] France ................................ 84 08376

[51] Int. Cl.$^4$ ............................................ C07C 148/00
[52] U.S. Cl. ........................................ 568/39; 568/45; 568/50; 568/55; 568/56
[58] Field of Search ..................... 568/45, 39, 50, 55, 568/56

[56] References Cited

U.S. PATENT DOCUMENTS

| | | | |
|---|---|---|---|
| 3,081,354 | 3/1963 | Gaertner et al. ...................... | 568/45 |
| 3,522,314 | 7/1970 | Warner .................................. | 568/39 |
| 3,872,058 | 3/1975 | Gresham ............................... | 524/792 |
| 4,266,080 | 5/1981 | Falk et al. ............................. | 568/50 |
| 4,517,384 | 5/1985 | Brace .................................... | 568/27 |

FOREIGN PATENT DOCUMENTS

| | | |
|---|---|---|
| 2856616 | 7/1979 | Fed. Rep. of Germany . |
| 2111253 | 6/1972 | France . |
| 2416222 | 8/1979 | France . |

OTHER PUBLICATIONS

Derwent Abstract of French patent No. 2,516,920, published 05/1983 (Inst. Nat.).

*Primary Examiner*—Mary E. Ceperley
*Attorney, Agent, or Firm*—Browdy and Neimark

[57] ABSTRACT

The invention relates to non ionic fluorinated compounds having the formula $R_FC$ hd $2H_4S(R)H$, wherein R designates a $C_2H_4X$ unit with X=O or S, or a chain exclusively comprising several such units, and two consecutive units can be identical or different, and $R_F$ is a perfluorinated alkyl group exclusive of compounds having the formula:

$$R_FC_2H_4SC_2H_4OH, R_FC_2H_4S(C_2H_4O)_2H \text{ and } R_F(C_2H_4S)_2H$$

and the mixtures of such compounds, in particular, the mixtures of the above defined products differing from one another by the length of their perfluorinated chain, but having the hydrophilic portion of the molecule identical from one product to the other.

To obtain them, a compound having the formula $R_FC_2H_4SH$ is reacted on an ethylene or polyethylene glycol monochlorhydrin; the alcohol function of the resulting product is also converted to thiol function and then the so obtained product is reacted on such a monochlorohydrin and the resulting alcohol function is again transformed to thiol function, and so on, up to obtaining the desired number of $C_2H_4O$ and/or $C_2H_4S$ groups.

Application as non ionic surfactant agent.

3 Claims, No Drawings

NOVEL NON IONIC FLUORINATED COMPOUNDS, THEIR PROCESS OF PREPARATION AND APPLICATIONS THEREOF AS SURFACTANTS

This application is a continuation of application Ser. No. 738,701 filed May 29, 1985, now abandoned.

This invention relates to novel compounds having the following general formula:

$$R_FC_2H_4S(R)H,$$

where R designates a $C_2H_4X$ unit (with X=O or S), or a chain exclusively comprising several of such units, two consecutive units being identical or different, and $R_F$ is a perfluorinated alkyl group; the invention also covers mixtures of such compounds, in particular, the mixtures of the products defined above differing from one another by the length of the perfluorinated chain thereof but having the hydrophilic portion of the molecule identical from one product to the other.

The only known products of this family have the following formulae:

$$R_FC_2H_4SC_2H_4OH,$$

$$R_FC_2H_4S(C_2H_4O)_2H \text{ and}$$

$$R_F(C_2H_4S)_2H$$

The new compounds of the invention present interesting surfactant properties.

Since many years, surfactants have been submitted to many experiments. Recently stress was laid on the necessity of possessing defined surfactants to obtain stable self-emulsifying systems composed of two emulsifying products, the one being more hydrophilic and the other more hydrophobic (or lipophilic). One can then adjust the hydrophilic/hydrophobic balance (HLB) so as to obtain maximum stability for the emulsion. Moreover, for certain uses, it is necessary to have non ionic surfactants available.

The compounds and mixtures of this invention meet such needs and constitute novel non ionic surfactants with a well defined hydrophilic portion.

The preparation of such compounds was guided by the following two criteria:

the requirement of working on industrially available starting products;

the prepared products must have a perfectly defined hydrophilic portion and must belong to homogeneous series to permit adjustment of various parameters such as HLB, the cloud point.

The object of this invention is thus a process for preparation of such compounds and mixtures according to a particularly supple synthesis giving products having the desired number and in particular a high number of ethylene oxide units.

Thus, according to the invention $R_FC_2H_4SH$ is reacted on several ethylene or polyethylene glycol monochlorohydrins defined according to the following scheme:

$$R_FC_2H_4SH \xrightarrow[Na]{EtOH} R_FC_2H_4SNa \xrightarrow{Cl(C_2H_4O)_nH} R_FC_2H_4S(C_2H_4O)_nH$$

with particularly $R_F = C_2H_5$, $C_4F_9$, $C_6F_{13}$, $C_8F_{17}$ with particularly n = (1,2,3,4)

to obtain a first defined product. Thus, it is possible to obtain the whole of a range of defined products with yields of 70–80%.

$R_FC_2H_4SH$ is itself easily obtained according to the following scheme:

$$R_FC_2H_4I + (NH_2)_2C=S \xrightarrow{\text{absolute EtOH}}$$

$$R_FC_2H_4SC(NH_2)=\overset{\oplus}{N}H_2, \overset{\ominus}{I} \xrightarrow{NaOH,aq.} R_FC_2H_4SH$$

wherein $R_FC_2H_4I$ is a product obtained industrially by fractionation of the telomerization product of tetrafluoroethylene and perfluoroethyl iodide.

To increase the number of ether units, it is proceeded as previously by means of a corresponding thiol by replacing the alcohol function of the previously synthetised product by the thiol function which is reacted again on ethylene or polyethylene monochlorohydrins defined according to the following scheme:

$$R_FC_2H_4S(C_2H_4O)_nH \quad (A)$$

I $\begin{cases} a = HBr, (NH_2)_2C=S \\ \text{or} \\ b = \text{Tos Cl/pyridine}, (NH_2)_2C=S/NaOH \end{cases}$ $$R_FC_2H_4S(C_2H_4O)_{n-1}C_2H_4S \text{ H} \quad (B)$$

II $\begin{cases} \text{EtO Na} \\ Cl(C_2H_4O)_n, H \text{ where n} = (1,2,3 \text{ or } 4) \end{cases}$ $$R_FC_2H_4S(C_2H_4O)_{n-1}C_2H_4S(C_2H_4O)_{n'}H \quad (C)$$

to obtain a second defined product possessing two thioether units. One can thus obtain a second range of defined products.

The same scheme can on its turn be applied to the product (C).

The mode Ia will preferably be applied when n=1, the mode II preferably when n>1.

The obtained products are liquids, the longest ones are solids with a low melting point.

They can be purified by vacuum distillation or simple filtration on silica column.

If an analogous process is applied to a mixture of products of the form $R_FC_2H_4SH$ formed from thiols differing from one another by the lengths of their perfluorinated chain $R_F$ a mixture of products with well defined hydrophilic portion will be obtained.

The essential advantage of the process is therefore its suppleness. Due to the proton of a thiol being much more movable than that of an alcohol, on the one hand, and on the other hand, due to the chlorohydrins with short chains (n≦4) being commercial, it results that it is easier, in order to obtain a monodispersed compound with a given hydrophilic chain, to proceed by successive additions of ethylene glycol units. The yields are thus higher and since moreover the first elements in the family are easily purifiable, the elements having a large number of ethylene oxide units (in particular, more than six units) become easily accessible.

This invention also relates to the applications of the products and mixtures according to the invention, in particular, as non ionic surfactant agents; due to their surfactant properties, the compounds according to the invention can be notably used as additives for thermosetting varnishes. They can also be used as emulsifiers to form micro-emulsions, notably with fluorinated or perfluorinated carbides, for example, with perfluorodecaline, F-alkylethenes, perfluoroalkylamines (type "FC 43" or "FTPA"), bisperfluoroalkylethenes, di(F-2-alkyl)-thioethanes ($R_F C_2 H_4 S C_2 H_4 R'_F$) and any other type of emulsion or micro-emulsion wherein fluorinated or not fluorinated compounds of pharmacological or biological use are invovled.

Micro-emulsion designates optically isotropic limpid and thermodynamically stable solutions composed of fluorocarbide, water and surfactant in variable proportions as was described in French patent No. 80 22875. Due to the possibility of adjusting at will the hydrophilic/hydrophobic balance of the surfactant, it was determined that there exist relative concentration ranges of these three constituents for which a stable micro-emulsion is obtained at a given temperature.

The following examples will make better appear the scope and interest of the invention.

EXAMPLE 1

$C_6F_{13}C_2H_4SC_2H_4OH$

In a two-liter reactor swept by an argon stream the ethylate is prepared from 18.9 g of sodium (0.825 mole) in 750 ml of absolute ethanol. 285 g of thiol $C_6F_{13}C_2H_4SH$ (0.75 mole) are introduced dropwise. A clear yellow liquid is obtained. It is then cooled with a cold water bath, then there is added dropwise 0.75 mole of 2-chloro-ethanol. A white precipitate of sodium chloride is formed. To complete the reaction, it is proceeded to reflux for 3 hours. It is allowed to cool, hydrolyzed with 10 cm³ of permutated water, filtered to separate sodium chloride, dried on magnesium sulfate, filtered, the solvent is removed and then it is distillated.

A product is obtained, presenting a B.P.=130°–133° C./18 mm Hg with a yield of 72%.

The product was analyzed by G.P.C. and proton NMR.

Purity through chromatography: 98.6%.
Proton NMR

| Unit | δ (ppm)/TMS | Intensity |
| --- | --- | --- |
| $CH_2O$ | 3.8 | 2 |
| $CH_2S$ | 2.77 | 4 |
| $CH_2$ | 2.3 | 2 |

The following products were prepaed in an analogous manner:
$R_F C_2 H_4 S(C_2 H_4 O)_n H$ by using different thiols $R_F C_2 H_4 SH$ and different chlorohydrins $Cl(C_2 H_4 O)_n H$.

| $R_F$ | n | B.P. °C./mm Hg | yield % | Purity by G.P.C. % |
| --- | --- | --- | --- | --- |
| $C_6F_{13}$ | 1 | 130–133/18 | 72 | 98.6 |
| $C_6F_{13}$ | 2 | 118–120/1.3 | 76.5 | 98.5 |
| $C_6F_{13}$ | 3 | 137–139/0.7 | 86 | 95.2 |
| $C_6F_{13}$ | 4 | 173–175/10.9 | 69.5 | 89.8 |
| $C_2F_5$ | 1 | 85–90/20 | 80 | 97.8 |
| $C_2F_5$ | 2 | 80–85/1.4 | 82 | 98.5 |
| $C_2F_5$ | 3 | 110/1.4 | 83 | 96.8 |
| $C_4F_9$ | 1 | 70/1.3 | 86.5 | 98.6 |
| $C_4F_9$ | 2 | 105–110/1.45 | 79 | 98.5 |
| $C_4F_9$ | 3 | 125/1,2 | 75 | 97.9 |

EXAMPLE 2

$C_6F_{13}C_2H_4SC_2H_4SH$

In a one-liter ground stopper Erlenmeyer swept by an argon stream, equipped with a refrigerant and magnetic stirring, there is put 0.05 mole of alcohol $C_6F_{13}C_2H_4SC_2H_4OH$, 0.05 mole of thiourea and 0.15 mole of HBr at 48%. The whole of it is heated to 100° C. for 20 hours under stirring. A precipitate is formed which adheres to the walls. It is allowed to cool and then there is added a sodium hydroxide solution prepared from 0.15 mole in 600 ml of water and thereafter it is again heated for two hours in reflux.

It is cooled with an icy water bath, then acidified with hydrochloric acid N. It is extracted by methylene chloride, the organic layer is washed with water, decanted, dried on magnesium sulfate and then the solvent is removed and it is distilled.

A product is obtained, presenting a B.P. of 125°–127° C./18 mm Hg with a yield of 64%.

Purity through chromatography: 94.9%.

EXAMPLE 3

$C_6F_{13}C_2H_4SC_2H_4OC_2H_4SH$

1. Synthesis of tosylate.

There is put 0.25 mole of alcohol $C_6F_{13}C_2H_4SC_2H_4OC_2H_4OH$ and 1 mole of pyridine into a two-liter reactor equipped with a stirring device, a refrigerant overlaid by a calcium chloride guard. It is cooled at 10° C. and there is added by means of a solid ampoule and by fraction, 0.3 mole of p-toluene sulfonyl chloride in about 30 minutes, so as to maintain the temperature lower than 20° C.

The mixture is then stirred for 4 hours at that temperature and then there is added a solution of hydrochloric acid prepared from 150 ml of acid 12N in 1.5 l of water.

There is extracted by methylene chloride, it is decanted, the organic phase is dried on magnesium sulfate, it is filtered and then the solvent is removed. The obtained tosylate is a viscous liquid which is used as such for the remainder of the synthesis.

Yield: 99%.

2. Passing to thiol.

There is introduced the preceding tosylate (0.247 mole), 0.37 mole of thiourea and 400 ml of absolute methanol into a one-liter reactor equipped with a refrigerant, stirring device, an ampula and swept by an argon stream. The mixture is heated to ethanol reflux for 20 hours. It is allowed to cool and the ethanol is then removed.

The preceding residue is put into an inert one-liter reactorand there is added 200 ml of water and then, it is heated under stirring to 70° C. At this temperature, 13.8 g of sodium hydroxide is added into 200 ml of water; it is held for two hours at this temperature. It is cooled, the medium is acidified with HCl N, it is extracted by methylene chloride, the organic layer is dried, the solvent is removed and then, it is distilled.

A product is obtained having a B.P.=155°–156° C./18 mm Hg with a yield of 59%.

The product is analyzed by chromatography and proton NMR.

Purity through chromatography: 96%.
Proton NMR:

| Unit | δ (ppm)/TMS | Intensity |
|---|---|---|
| $CH_2O$ | 3.61 | 4 |
| $CH_2S$ | 2.76 | 6 |
| $CH_2$ | 2.5 | 2 |
| SH | 1.58 | 1 |

In the same manner, $C_6F_{13}C_2H_4S(C_2H_4O)_2C_2H_4SH$ is prepared from $C_6F_{13}C_2H_4S(C_2H_4O)_3H$.
B.P.=124°–125° C./0.5 mm Hg with a yield of 86%.
Purity through chromatography: 93.4%.
Proton NMR:

| Unit | δ ppm/TMS | Intensity |
|---|---|---|
| $CH_2O$ | 3.63 | 8 |
| $CH_2S$ | 2.76 | 6 |
| $CH_2$ | 2.51 | 2 |
| SH | 1.58 | 1 |

EXAMPLE 4

$C_6F_{13}C_2H_4SC_2H_4S(C_2H_4O)_3H$

An ethylate is prepared in an inert 250 ml reactor from 0.077 mole of sodium in 100 ml of absolute ethanol. When all the sodium is etched, there is added 0.07 mole of thiol $C_6F_{13}C_2H_4SC_2H_4SH$ for 15 minutes. There is no temperature increase during the flowing. It is stirred for 15 minutes after completing the flowing, then 0.07 mole of chlorohydrin is added during 15 minutes. It is then heated for 3 hours to the ethanol to reflux. It is cooled and then, hydrolyzed with 20 cc of permutated water to eliminate sodium ethylate in excess. It is extracted by methylene chloride, the organic layer is dried, it is filtered and the solvent is removed before distillation.

A product is obtained having a B.P. of 160°–162° C./0.2 mm Hg with a yield of 43%.
Purity through chromatograph: 98.5%.
Proton NMR:

| Unit | δ (ppm)/TMS | Intensity |
|---|---|---|
| $CH_2O$ | 3.65 | 10 |
| $CH_2S$  | 2.80 | 10 |
| $CH_2$ | | |

In the same manner, $C_6F_{13}C_2H_4SC_2H_4OC_2H_4S(C_2H_4O)_2H$ is prepared from $C_6F_{13}C_2H_4SC_2H_4OC_2H_4SH$ and $Cl(C_2H_4O)_2H$.
B.P.=157°–158° C./0.12 mm Hg with a yield of 72%.
Purity through chromatography: 97.5%.
Proton NMR:

| Unit | δ ppm/TMS | Intensity |
|---|---|---|
| $CH_2O$ | 3.68 | 10 |
| $CH_2S$ | 2.75 | 8 |
| $CH_2$ | 2.38 | 2 |
| OH | 2.53 | 1 |

In an analogous manner, $C_6F_{13}C_2H_4S(C_2H_4O)_2C_2H_4SC_2H_4OH$ is prepared from $C_6F_{13}C_2H_4S(C_2H_4O)_2C_2H_4SH$ and $ClC_2H_4OH$.
B.P.=165°–170° C./10.6 mm Hg with a yield of 78%.
Purity through chromatography: 99.7%.
Proton NMR:

| Unit | δ ppm/TMS | Intensity |
|---|---|---|
| $CH_2O$ | 3.63 | 10 |
| $CH_2S$ | 2.72 | 8 |
| $CH_2$ | 2.35 | 2 |

By proceeding in the same manner, $C_6F_{13}C_2H_4S(C_2H_4O)_3H$ is prepared from $C_6F_{13}C_2H_4SC_2H_4OC_2H_4SH$ and $Cl(C_2H_4O)_3H$.
B.P.=191°–193° C./0.3 mm Hg.
Purity through chromatography: 99%.

EXAMPLE 5

Mixtures of products in the form $R_FC_2H_4S(C_2H_4O)_3H$.

It is proceeded as in Example 1 by replacing thiol $C_6F_{13}C_2H_4SH$ by an industrial cut corresponding to a mixture A of thiols in the following proportions (analysis in C.P.G.):

| 30.5% | $C_6F_{13}C_2H_4SH$ |
|---|---|
| 34.3% | $C_8F_{17}C_2H_4SH$ |
| 27.3% | $C_{10}F_{21}C_2H_4SH$ |
| 4.2% | $C_{12}F_{25}C_2H_4SH$ |

Ethylate is prepared in a 500 ml reactor swept by an argon stream from 5.06 g (0.22 mole) in 200 ml of absolute ethanol. When all sodium is etched the temperature is decreased and it is maintained in water bath at the ambient temperature and 96 g of the mixture of thiols A is added thereto. It is stirred for 15 minutes and 33.7 g of chlorhydrin (0.2 mole) are introduced thereinto. It is heated for 3 hours to ethanol reflux.

The mixture is colored brown and NaCl precipitates. It is hydrolyzed with 10 cc of permutated water, the sodium chloride is filtered and ethanol is removed.

The residue is taken again to chloroform, it is washed with water and dried on magnesium sulfate. It is filtered and then, the solvent is removed. The very colored residue is distilled under 0.2 mm Hg. There is obtained (B.P./0.2 mm Hg=132°–167° C.) 122.4 g of a product of the consistency of a wax, analysis of which by G.P.C. reveals that it contains:

| 33.8% | $C_6F_{13}C_2H_4S(C_2H_4O)H$ |
|---|---|
| 35.4% | $C_8F_{17}C_2H_4S(C_2H_4O)_3H$ |
| 24.8% | $C_{10}F_{21}C_2H_4S(C_2H_4O)_3H$ |
| 3.1% | $C_{12}F_{25}C_2H_4S(C_2H_4O)_3H$ |

II. Examples of use

1. As surfactant additives for thermosetting varnishes.

Test No. 1

Two parts of $C_6F_{13}C_2H_4S(C_2H_4O)_3H$ are added to 1000 parts of thermosetting varnish "IRDALON 300.1" prepared according to Example 1 of French patent application published under No. 2523590.

The composition of the so obtained coating is spread out on a polycarbonate plate (LEXAN manufactured by General Electric) of $100 \times 100 \times 2$ (mm) by immersion (immersion speed: 120 mm/minute), and then hardened by heating to 120° C. for 75 minutes.

The coated plate is then submitted to abrasion test ASTM D 1044 TABER by means of a TABER abrasimeter.

Such test consists of measuring the percentage of optical haze by means of a "Hazemeter" after passing the sample below two abrasive ballasted runners for a determined number of revolutions.

In this example, the load on the abrasive runners was 1000 g and the number of revolutions equal to 100.

The percentage of haze measured was 1.1% as against 3.5% for a reference plate coated with a varnish not containing such surfactant agent and 30% for an uncoated plate.

Test No. 2

There are added 2 parts of $C_6F_{13}C_2H_4SC_2H_4SC_2H_4O_2H$ to 1000 parts of thermosetting varnish "IRDALON 300.1".

Thereafter, it is proceeded in the same manner as in Test No. 1. The haze percentage was here 0.9%.

2. For micro-emulsions.

This Example shows that it is possible to obtain micro-emulsions of fluorocarbides by using a non ionic fluorinated surfactant according to the invention.

As a matter of fact, it was found that there are relative concentration zones of the three constituents: water, fluorocarbide, surfactant agents within which a stable micro-emulsion is obtained at a given temperature. It is therefore suitable to determine, for a given fluorocarbide, the ternar diagram having such concentration zones which procure a limpid and stable micro-emulsion at the desired temperature. Such zones may be of two types, i.e. those wherein the most abundant constituent by volume is water (oil in water type) and those wherein the most abundant constituent by volume is fluorocarbide (water in oil type).

The above examples of ternar mixtures show versatility of the systems as regards temperature and their possible interest in biological applications.

Micro-emulsions of the "oil in water" type.

EXAMPLE 1

Preparation of a micro-emulsion.
$H_2O/C_8F_{17}C=CH_2/C_6F_{13}C_2H_4S(C_2H_4O)_3H$ stable at 25° C.

There is added into a test tube 1.0 g of $C_6F_{13}C_2H_4S(C_2H_4O)_3H$, 7.1 g of $H_2O$ and 1.9 g of $C_8F_{17}CH=CH_2$.

After mechanical stirring for a few minutes, and short heating to a temperature higher than 25° C., the mixture was put into a bath, thermostat at 25° C.; a limpid solution stable at this temperature was obtained.

EXAMPLE 2

Preparation of a micro-emulsion.
$H_2O/C_8F_{17}C=CH_2/C_6F_{13}C_2H_4S(C_2H_4O)_3H$ stable at 37° C.

There is added into a test tube 1.5 g of $C_6F_{13}C_2H_4S(C_2H_4O)_3H$, 6.0 g of $H_2O$ and 2.5 g of $C_8F_{17}CH=CH_2$.

After mechanical stirring for a few minutes and short heating to a temperature higher than 37° C., the mixture was placed into a bath with thermostat at 37° C.; a limpid solution stable at this temperature was obtained.

EXAMPLE 3

Preparation of a micro-emulsion.
$H_2O/C_8F_{17}CH=CH_2/C_6F_{13}(C_2H_4S)_2(C_2H_4O)_3H$ stable at 25° C.

There was added into a test tube 1.5 g of $C_6F_{13}(C_2H_4S)_2(C_2H_4O)_3H$, 4.1 g of $H_2O$ and 4.4 g of $C_8F_{17}CH=CH_2$.

After mechanical stirring and heating to a temperature higher than 25° C. for a few minutes, the mixture was placed into a bath with thermostat at 25° C.; a limpid solution stable at the this temperature was obtained.

EXAMPLE 4

Preparation of a micro-emulsion.
$H_2O$/perfluorodecaline/$C_6F_{13}C_2H_4S(C_2H_4O)_3H$ stable at 30° C.

There was added into a test tube 1.01 g of $C_6F_{13}C_2H_4S(C_2H_4O)_3H$, 5.58 g of $H_2O$ and 3.41 g of perfluorodecaline.

After mechanical stirring and heating to a temperature higher than 30° C. for a few minutes the mixture was placed into a bath with thermostat at 30° C.; a limpid solution stable at this temperature was obtained.

EXAMPLE 5

Preparation of a micro-emulsion.
$H_2O/C_4F_9CH=CHC_4F_9/C_6F_{13}C_2H_4S(C_2H_4O)_3H$ stable at 20° C.

There was added into a test tube 1.53 g of $C_6F_{13}C_2H_4S(C_2H_4O)_3H$, 5.95 g of $H_2O$ and 2.52 g of $C_4F_9CH=CHC_4F_9$.

It was proceeded according to the previously defined operational mode and a micro-emulsion stable at 20° C. was obtained.

EXAMPLE 6

Preparation of a micro-emulsion.
$H_2OC_8F_{17}CH=CH_2/C_6F_{13}C_2H_4S(C_2H_4O)_4H$ stable at 20° C.

There was added into a test tube 1.5 g of $C_6F_{13}C_2H_4S(C_2H_4O)_4H$, 5.0 g of $H_2O$ and 3.5 g of $C_8F_{17}CH=CH_2$. It was proceeded according to the above defined operational mode and a micro-emulsion stable at 20° C. was obtained.

Micro-emulsions of the "water in oil" type.

EXAMPLE 1

Preparation of a micro-emulsion.
$H_2O$/perfluorodecaline/$C_6F_{13}C_2H_4S(C_2H_4O)_3H$ stable at 30° C.

There was added into a test tube 3.0 g of $C_6F_{13}C_2H_4S(C_2H_4O)_3H$, 0.5 g of $H_2O$ and 6.5 g of perfluorodecaline.

It was proceeded according to the above defined operational mode and a micro-emulsion stable at 30° C. was obtained.

EXAMPLE 2

Preparation of a micro-emulsion.

$H_2O/C_8F_{17}CH=CH_2/C_6F_{13}(C_2H_4S)_2(C_2H_4O)_3H$ stable at 30° C.

There was added into a test tube 3.0 g of $C_6F_{13}C_2H_4S(C_2H_4O)_3H$, 0.5 g of $H_2O$ and 6.5 g of $C_8F_{17}CH=CH_2$.

It was proceeded according to the above defined operational mode and a micro-emulsion stable at 30° C. was obtained.

EXAMPLE 3

Preparation of a micro-emulsion.
$H_2O/C_8F_{17}CH=CH_2/C_6F_{13}C_2H_4S(C_2H_4O)_2C_2H_4S(C_2H_4O)_3H$ stable at 20° C.

There was added into a test tube 3.7 g of: $C_6F_{13}C_2H_4S(C_2H_4O)_2C_2H_4S(C_2H_4O)_3H$, 1.3 g of $H_2O$ and 5.0 g of $C_8F_{17}CH=CH_2$.

It was proceeded according to the above defined operational mode and a micrio-emulsion stable at 20° C. was obtained.

EXAMPLE 4

Preparation of a micro-emulsion.
$H_2O/$perfluorodecaline$/C_6F_{13}C_2H_4SC_2H_4OC_2H_4S(C_2H_4O)_3H$ stable at 25° C.

There was added into a test tube 2.0 g of $C_6F_{13}C_2H_4SC_2H_4OC_2H_4S(C_2H_4O)_3H$, 1.5 g of $H_2O$ and 6.5 g of perfluorodecaline.

It was proceeded according to the above defined operational mode and a micro-emulsion stable at 25° C. was obtained.

EXAMPLE 5

Preparation of a micro-emulsion.
$H_2O/C_8F_{17}CH=CH_2/C_6F_{13}C_2H_4S(C_2H_4O)_4H$ stable at 20° C.

There was added into a test tube 3.5 g of $C_6F_{13}C_2H_4S(C_2H_4O)_4H$, 1.0 g of $H_2O$ and 5.5 g of $C_8F_{17}CH=CH_2$.

It was proceeded according to the above defined operational mode and a micro-emulsion stable at 20° C. was obtained.

It will be understood that this invention was only described in a purely explanatory and not at all limitative manner and that any useful modification can be entered thereinto without departing from its scope.

We claim:

1. A process for preparing a surfactant having the formula:

$$R_FC_2H_4S(R)H$$

in which

R designates a chain exclusively consisting of at least 2 identical or different units of the formula $C_2H_4X$ wherein $X=O$ or $X=S$ and $R_F$ is a perfluorinated $C_2$–$C_{12}$ alkyl group, comprising the steps of:
(a) reacting a compound having the formula $R_FC_2H_4S(R')H$ wherein $R'$ is a sulfur-hydrogen bond or a chain exclusively consisting of one or more identical or different units of $C_2H_4X$ wherein $X=O$ or $X=S$ and X when bound to H is S, $R'$ having at least one less $C_2H_4X$ unit than does R and $R_F$ has the meaning given above, with ethylene or polyethylene glycol monochlorohydrin, in the presence of ethanol and sodium to obtain a first product having a terminal alcohol function; and
where said first product has less $C_2H_4X$ units than in R:
(b) replacing the terminal alcohol function of the product of the previously performed step with a thiol function and reacting the thiol product resulting therefrom with ethylene or polyethylene glycol monochlorohydrin in the presence of ethanol and sodium; and
(c) repeating step (b) upon the product thereof until said surfactant is obtained.

2. The method of claim 1, wherein the replacement of the alcohol function by a thiol function is performed by reacting said product with thiourea in the presence of HBr.

3. The method of claim 1, wherein said first product has less $C_2H_4X$ units than in R.

* * * * *